United States Patent [19]

Suhadolnik

[11] Patent Number: 4,990,498
[45] Date of Patent: Feb. 5, 1991

[54] 2- AND 8-AZIDO(2'-5')OLIGOADENYLATES AND ANTIVIRAL USES THEREOF

[75] Inventor: Robert J. Suhadolnik, Roslyn, Pa.

[73] Assignee: Temple University-of the Commonwealth System of Higher Education, Philadelphia, Pa.

[21] Appl. No.: 186,414

[22] Filed: Apr. 26, 1988

[51] Int. Cl.$^5$ .............................................. C07H 17/02
[52] U.S. Cl. ..................................... 514/47; 514/48; 536/27; 536/28
[58] Field of Search ..................... 536/27, 28; 514/47, 514/48

[56] References Cited

PUBLICATIONS

Knowles, "Photogenerated Reagents for Biological receptor-Site Labeling," Acct. Chem Res. 5:155-160 (1972).
Hoyer et al., "The Use of Photoaffinity Probes to Elucidate Molecular Mechanisms of Nucleotide-Tegulated Phenomena," Ann. N.Y. Acad. Sci. 346:280-381 (1980).
Evans et al., "Photoaffinity Labeling of a Viral Induced Protein from Tobacco," J. Biol. Chem. 260:7800-7804 (1985).
Hegyi et al., "Photoaffinity Labeling of the Nucleotide Binding Site of Actin," Biochemistry 25:5793-5798 (1986).
Malkinson et al., "Changes in Pulmonary Adenosine Triphosphate-binding Proteins Detected by Nucleotide Photoaffinity Labeling Following Treatment of Mice With The Tumor-Modulatory Agent Butylated Hydroxytoluene," Biochemistry 25:5793-5798 (1986).
Garin et al., "Identification of Amino Acid Residues Photolabeled with 2-Azido [$\alpha$-$^{32}$P] adenosine Diphosphate in the $\beta$ Subunit of Beef Heart Mitochondrial F$_1$-ATPase," Biochemistry 25:4431-4437 (1986).
Lundari et al., "Mapping of Nucleotide-depleted Mitochondrial F$_1$-ATPase wtih 2-Azido-[$\alpha$-$^{32}$P] adenosine Diphosphate," J. Biol. Chem. 262:15172-15181 (1987).
Boulay et al., "Photoaffinity Labeling of Mitochondrial Adenosinetriphosphate by 2-Azidoadenosine 5'-[$\alpha^{32}$P-]Diphosphate," Biochemistry 24:7372-7379 (1985).
Li et al., "2- and 8-AzidoATP: Photoaffinity Labelling of 2-5A Synthetase, Enzymatic Synthesis of 2- and 8-Azido Analogs of 2-5A for Use as Photoaffinity Probes of RNase L", J. Inter F. Res. 7:829 (Dec. 1987) (abstract).
Woody et al., "Characterization of a Photoaffinity Analog of UTP, 5- Azido-UTP for Analysis of the Substrate Binding Site of E. Coli RNA Polymerase," Biochim. Biophys. Res. Commun. 150:917-924 (Feb. 15, 1988).
Li et al., "2',5'-8-Azidoadenylate Trimer 5'-Triphosphate (2,5-8N$_3$p$_3$A$_3$): Enzymatic Synthesis, Biological Properties and Photoaffinity Labelling of RNase L," Federation Proceedings 46:2084 (May 1, 1987) (abstract).

Primary Examiner—Richard L. Raymond
Attorney, Agent, or Firm—Seidel, Gonda, Lavorgna & Monaco

[57] ABSTRACT

Compounds of the formula (Abstract continued on next page.)

-continued

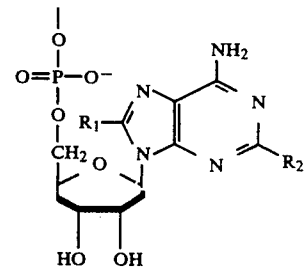

-continued

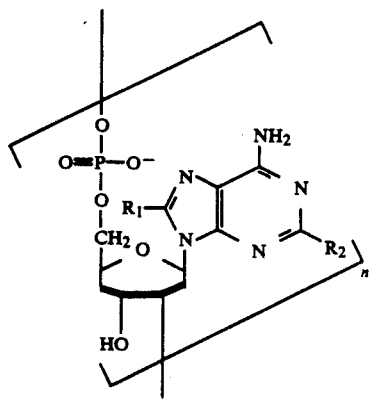

wherein m is 0, 1, 2 or 3; n is 0, 1, 2 or 3; and each $R_1$ and each $R_2$ is, independently of each other $R_1$ and $R_2$, hydrogen or $N_3$, provided at least one $R_1$ or $R_2$ is $N_3$; and water soluble salts thereof. Compounds of the formula activate RNase L, leading to the cleavage of viral mRNA or rRNA, thereby inhibiting viral protein synthesis. They also have activity against plant-infecting viruses. The compounds, upon UV irradiation, form nitrene free radical intermediates which are capable of covalently photoinserting into (or cross-linking) biological molecules.

24 Claims, 5 Drawing Sheets

FIG. 4A

Lane: 1 2 3 4 5 6

UV Irradiation: — + + + + +

Specifically Labelled
Proteins:

- 205

158  a→
109  b→                          - 116
                                 - 97.4
89   c→
80   d→
63   e→                          - 66

46   f→                          - 45

- 29

[α-$^{32}$P]8-N$_3$p$_3$A$_3$: + + + + + —

Added Nucleotide: — — p$_3$A$_3$ 2'-5' 3'-5' p$_3$A$_4$ [$^{32}$P]pCp
                              A$_3$  A$_3$

2- AND 8-AZIDO(2'-5')OLIGOADENYLATES AND ANTIVIRAL USES THEREOF

REFERENCE TO GOVERNMENT GRANT

The invention described herein was made, in part, in the course of work supported by National Institutes of Health Grants GM 27210 and CA 29545, and National Science Foundation Grant PCM 84-15002.

FIELD OF THE INVENTION

The invention relates to synthetic analogues of naturally occurring antiviral 2',5'-oligoadenylates wherein one or more of the hydrogens of the adenine ring is replaced by an azido group. The compounds have antiviral activity.

BACKGROUND OF THE INVENTION

The following representative abbreviations may be used herein:

SDS-PAGE: Sodium dodecylsulfate polyacrylamide gel electrophoresis.

HEPES: 4-(2-hydroxyethyl)-1-piperazine ethanesulfonic acid.

Poly(rI). poly(rC)-agarose: poly(inosinate). poly(cytidylate) double stranded polynucleotide covalently bound to agarose through poly(rI).

2-5A, 2',5'-oligoadenylate or $p3A_n$: Oligomer of adenylic acid with 2',5'-phosphodiester linkages and a 5' terminal triphosphate group.

AMP: 5'-adenylic acid or adenosine 5'-monophosphate.

ADP: Adenosine 5'-diphosphate.

ATP: Adenosine 5'-triphosphate. $A_2$, $A_3$ and $A_4$: Dimer, trimer and tetramer of AMP with 2',5'-phosphodiester linkages and without 5'-, 3'- or 2'-terminal phosphate groups.

$pA_3$, $ppA_3$ (or $p_2A_3$), $pppA_3$ (or $p_3A_3$) 5'-terminal mono-, di- and triphosphates of $A_3$.

2-azido-ATP or 2-N$_3$ATP: 2-azidoadenosine 5'-triphosphate.

2-Azido-ADP or 2-N$_3$ADP: 2-azidoadenosine 5'-diphosphate.

2-Azido-AMP or 2-N$_3$AMP: 2-azidoadenosine 5'-monophosphate.

8-Azido-ATP or 8-N$_3$ATP: 8-azidoadenosine 5'-triphosphate.

8-Azido-ADP or 8-N$_3$ADP: 8-azidoadenosine 5'-diphosphate.

8-Azido-AMP or 8-N$_3$AMP: 8-azidoadenosine 5'-monophosphate.

2,8-diazido-ATP or 2,8-N3ATP: 2,8-diazidoadenosine 5'-triphosphate.

2,8-diazido-ADP or 2,8-N$_3$ADP: 2,8-diazidoadenosine 5'-diphosphate.

2,8-diazido-AMP or 2,8-N$_3$AMP: 2,8-diazidoadenosine 5'-monophosphate.

x-N$_3$ATP: The group of azidonucleotides consisting of 2-azido-ATP, 8-azido-ATP and 2,8-diazido-ATP.

x-N$_3$ADP: The group of azidonucleotides consisting of 2-N3ADP, 8-N3ADP and 2,8-N3ADP.

x-N$_3$AMP: The group of azidonucleotides consisting of 2-N3AMP, 8-N3AMP and 2,8-N3AMP.

2-azido-p3A3 or p3(A2-azido)3 5'-O-triphosphoryl-(2-azidoadenylyl(2,-5,)2-azidoadenylyl(2,-5,)2-azidoadenosine.

8-azido-p3A3 or p3(A8-azido)3 5'-O-triphosphoryl-(8-azidoadenylyl(2'-5')8-azidoadenylyl(2'-5')8-azidoadenosine.

The symbols A$_2$-azido, A$_8$-azido, A$_{2,8}$-diazido and A, as used in representing the oligomers described herein, shall mean, respectively, 2-azidoadenylyl, 8-azidoadenylyl, 2,8-diazidoadenylyl and adenylyl moieties linked to each other by 2',5'-phosphodiester linkages, but without phosphate groups on the 2'-terminal moiety of the oligomer. For example, the compound 2-azidoadenylyl(2'-5')adenylyl(2'-5')8-azidoadenosine may be represented as A$_2$-azido AA$_8$-azido The 5'-triphosphate thereof, namely 5'-O-triphosphoryl-(2-azidoadenylyl)(2'-5')adenylyl(2'-5')8-azidoadenosine, may be represented as pppA$_{2\text{-azido}}$ AA$_8$-azido or $p3A_{2\text{-}azido}AA_{8\text{-}azido}$.

The symbol A$_{x\text{-}azido}$ as used in representing the oligomers described herein shall mean the group consisting of 2-azidoadenylyl, 8-azidoadenylyl and 2,8-diazidoadenylyl, as each is defined above.

The 2-5A system is widely accepted to be part of the antiviral mechanism of interferon and may also play a role in the regulation of cell growth. 2-5A synthesized from ATP by 2',5'-oligoadenylate synthetase [ATP: (2'-5')oligo(A)-adenylyltransferase (EC 2.7.7.19)]exerts its biological effects by binding to and activating its only known target enzyme, the unique 2-5A-dependent endoribonuclease, RNase L (EC 3.1.27). RNase L cleaves viral and cellular mRNA or rRNA, thereby inhibiting protein synthesis. Hovanessian et al, Eur. J. Biochem. 93:515–526 (1979); Kerr et al, Proc. Natl. Acad. Sci. USA. 75:256–260 (1978). It has been reported that 2-5A protects plant tissue from infection by tobacco mosaic virus. Devash et al, Science 216:415–416 (1982). It has also been reported that 2-5A inhibits avian myeloblastosis virus, Rous associated virus 2, and Moloney murine leukemia virus. Liu et al., Biochem. Biophys. Res. Commun. 145:291–297 (1987).

RNase L may not be the only target whose activity is modulated by 2-5A. The latter has also been implicated to be involved in the regulation of lymphocyte mitogenesis or cap methylation of viral mRNA through mechanisms different from RNase L activation.

Molecules containing azido groups form covalent bonds to proteins through reactive nitrene intermediates, generated by low intensity ultraviolet light. Knowles, Acct. Chem Res. 5:155–160 (1972); Hoyer et al., Ann. N.Y. Acad. Sci. 346:380–381 (1980). In particular 2- and 8-azido analogues of purine nucleotides have been used as site-directed photoprobes to identify nucleotide binding proteins in crude cell extracts. Evans et al., J. Biol. Chem. 260:7800–7804 (1985); Malkinson et al., Cancer Res. 46:4626–4630 (1986). 2- and 8-azido nucleotides have also been used to map nucleotide binding domains of purified proteins. Hegyi et al., Biochemistry 25:5793–5798 (1986); Garin et al., Biochemistry 25:4431–4437 (1986); Lunardi et al., J. Biol. Chem. 262:15172–15181 (1987). They have also been used to study enzyme kinetics of purified proteins. Boulay et al., Biochemistry 24:7372–7379 (1985). However, (2'-5')oligomers of 2- and 8-azido nucleotides have not been hitherto known.

SUMMARY OF THE INVENTION

Compounds of the present invention are useful in inhibiting viral infection in plants and animals. The compounds are of the formula

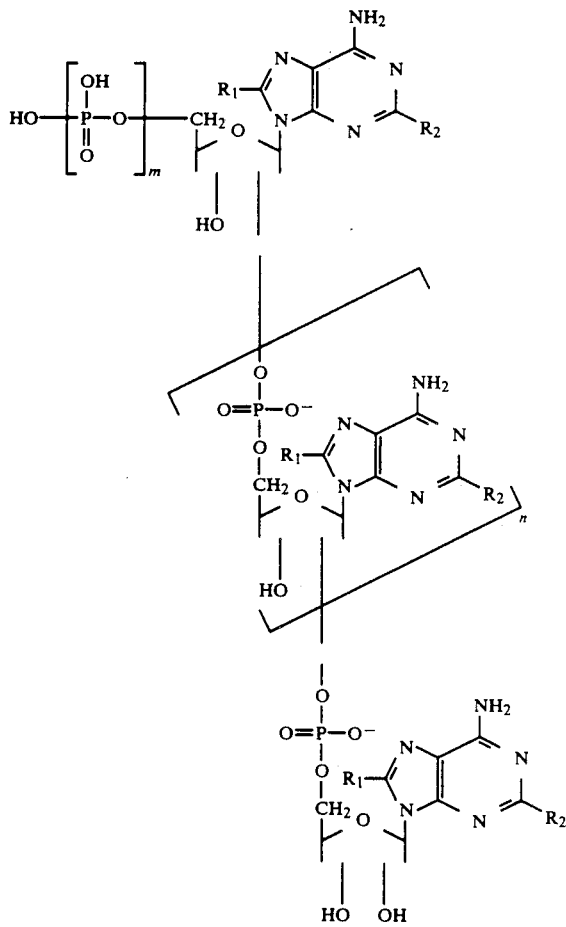

wherein m is an integer from 0 to 3; n is an integer from 0 to 3; and each $R_1$ and each $R_2$ is, independently of each other $R_1$ and $R_2$, hydrogen or $N_3$, provided at least one $R_1$ or $R_2$ is $N_3$. Also included in the invention are the water-soluble salts of the compounds of the above formula.

The invention also comprises a method of inhibiting viral infection in mammals or plants by administering an antiviral effective amount of a compound according to the above formula, or a water-soluble salt thereof.

DESCRIPTION OF THE FIGURES

FIG. 4A is an autoradiogram following SDS-PAGE of interferon treated L929 cell extracts incubated with [alpha-$^{32}$P]8-azido-$p_3A_3$ at $1 \times 10^{-6}$M in the absence (lanes 1 and 2) or presence of the following: $p_3A_3$ at $1 \times 10^{-4}$M (lane 3); $p_3A_3$ at $5 \times 10^{-4}$M (lane 4); or 3'-5'$A_3$ at $5 \times 10^{-4}$M (lane 5). The samples were UV irradiated (lanes 2–6) for 60 seconds at 0° C. prior to electrophoresis. Under identical experimental conditions, the L929 cell extract was incubated with $p_3A_4[^{32}P]pCp$ at $1 \times 10^{-8}$M (lane 6). Photolabelled proteins were detected by autoradiography.

DETAILED DESCRIPTION OF THE INVENTION

Figure 1:
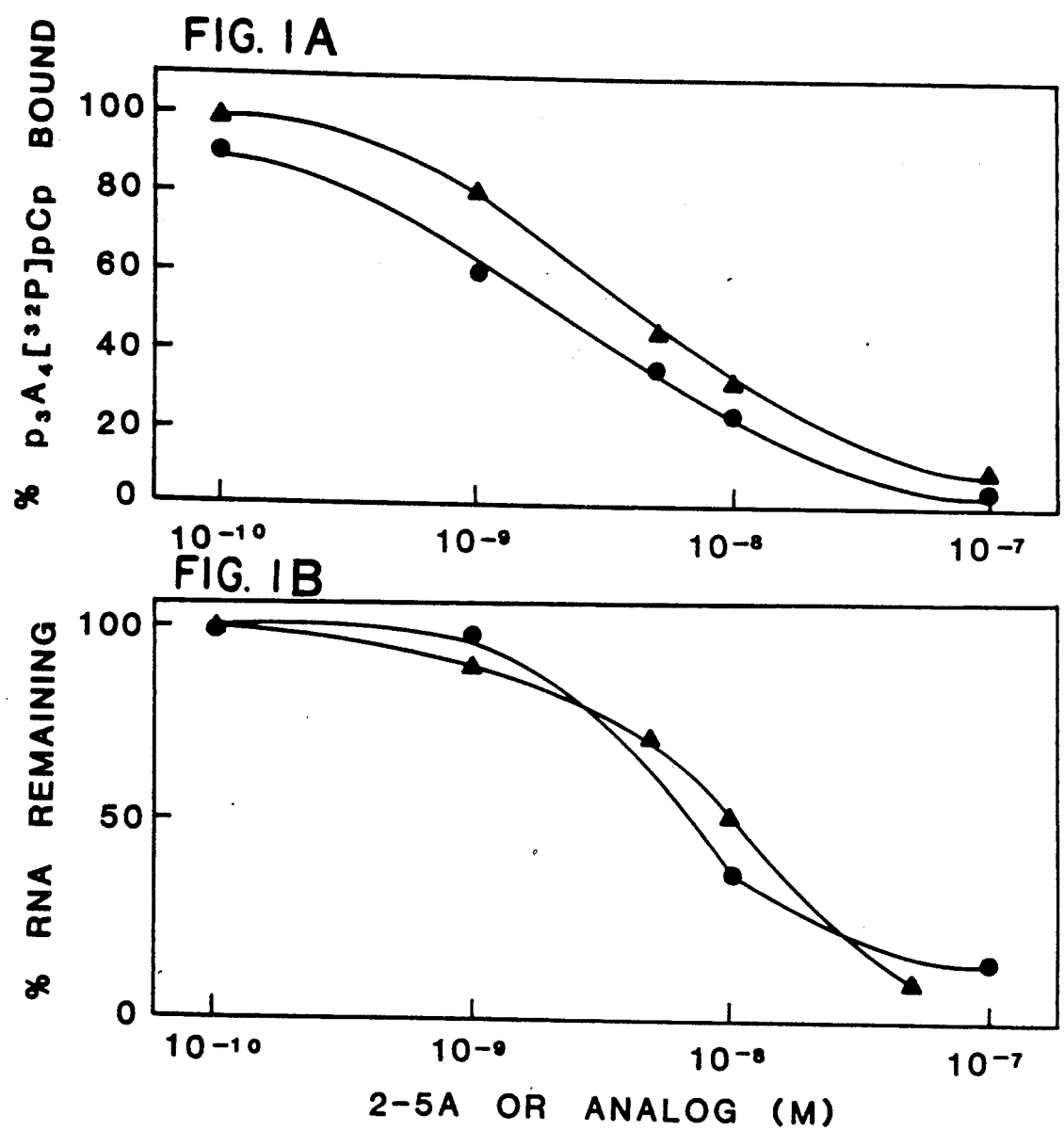
FIG. 1A is a plot of 8-azido-$p_3A_3$ (solid circle data points) competition with $p_3A_4[^{32}P]pCp$ for binding to RNase L in L929 cell extracts, compared to $p_3A_3$ (solid triangle data points) in a radiobinding assay.
FIG. 1B is a plot of 8-azido-$p_3A_3$ (solid circle data points) activation of partially purified RNase L from L929 cell extracts compared to $p_3A_3$ (solid triangle data points) in a core-cellulose assay.

The activation of the unique 2-5A-dependent endoribonuclease, RNas L, by 2',5'-oligoadehylates., and its hydrolysis of rRNA, tRNA and cellular and viral mRNA, is important in the inhibition of viral replication and regulation of cell growth. RNase L is known to be the substrate target for 2-5A. It is one of the chief functional enzymes of the interferon-induced biological cascade.

The compounds of the invention effectively bind to and activate RNase L. In particular, the (2'-5')2-azido trimer and (2'-5')8-azido-oligoadenylate trimer, i.e. 5'-O-triphosphoryl-(2-azidoadenylyl)(2'-5')2-azidoadenylyl(2'5')2-azidoadenosine and 5'-O-triphosphoryl-(8-azidoadenylyl)(2'-5')8-azidoadenylyl(2'-5')8-azidoadenosine, have biological activities almost identical to that of authentic 2-5A. This indicates that azido substitution on the C-2 or C-8 position, unlike bromo substitution on the C-8 position of 2-5A (Sarma et al., J. Am. Chem. Soc. 96:7337–7348 (1974); Lesiak et al., J. Med. Chem. 29: 1015–1022 (1986)), and unlike chloro substitution on the C-2 position (Hughes et al., Biochemistry 22:2127–2135 (1983)), does not alter the RNase L binding and activation ability of the molecule.

Unlike authentic 2-5A, the compounds of the invention, by virtue of the photosensitive azido group, readily form reactive nitrene radical intermediates (C-N ) upon exposure to low intensity ultraviolet light. The nitrene radical intermediate reacts with, and covalently photolabels, viral proteins and nucleic acid.

The compounds of the invention include, for example, the following, and their 5'-mono-, di- and triphosphates:

Oligomers of a single azidoadenylyl species, such as, for example:

$^A$2-azido$^A$2-azido$^A$2-azido or 2-azidoadenylyl(2'-5')2-azidoadenylyl(2'-5')2-azidoadenosine;

$^A$2-azido$^A$2-azido$^A$2-azido$^A$2-azido or 2-azidoadazidoadenosine;

$A_8$-azido$A_8$-azido$A_8$-azido or 8-azidoadenylyl(2'-5')8-azidoadenylyl(2'-5')8-azidoadenosine;

$A$8-azido$A$8-azido$A$8-azido$A$8-azido or 8-azidoadenylyl(2'-5')8-azidoadenylyl(2'-5')8-azidoadenylyl(2'-5')8azidoadenosine;

$A_{2,8}$-diazido$A$2,8-diazido$A$2,8-diazido or 2,8-diazidoadenylyl(2'-5')2,8-diazidoadenylyl(2'-5')2,8-diazidoadenosine;

$A_{2,8}$-diazido$A$2,8-diazido$A$2,8-diazido$A$2,8-diazido or 2,8-diazidoadenylyl(2'-5')2,8-diazidoadenylyl(2'-5')2,8-diazidoadenylyl(2'-5')2,8-diazidoadenosine.

Oligomers of AMP and a single azidoadenylyl species, such as, for example:

$A$2-azido$A$2-azido$A$ or 2-azidoadenylyl(2'-5')2-(2'-5')adenosine;

AA$_8$-azidoA$_8$-azido or adenylyl(2'-5')8-azidoadenylyl(2'-5')8-azidoadenosine.

Oligomers containing more than one azidoadenylyl species, such as, for example:

A$_2$-azidoA$_8$-azidoA$_2$-azido or 2-azidoadenylyl(2'-5')8-azidoadenylyl(2'-5')2-azidoadenosine.

Oligomers resulting from any combination of the monomers AMP, 2-azido-AMP, 8-azido-AMP and/or 2,8-diazido-AMP are possible, provided at least one such monomer incorporated into the oligomer is an azido-AMP species.

The compounds of the present invention are synthesized from azidoadenosine 5'-triphosphates or combinations thereof, or from azidoadenosine 5'-triphosphates and ATP. The latter provides a (2'-5')oligomer containing both adenylyl and azidoadenylyl moieties. The oligomers are synthesized from the nucleoside 5'-triphosphates with 2-5A synthetase from rabbit reticulocyte lysates. 2-5A synthetase for this purpose may also be obtained from L929 cells according to Lee, et al., Biochemistry 24:551–555 (1985), and from interferon-treated HeLa cells according to Baglioni et al., Biochemistry 18:1765–1770 (1979). The L929 cell line is a readily available immortalized murine lung cell line.

While highly purified forms of 2-5A synthetase have been used to synthesize authentic 2-5A, Wu et al., Biochemistry Internat. 6:207–216 (1983), such purified preparations are not suitable for preparing 2-5A analogues, including the instant (2'-5')azido-oligoadenylates. Thus it is preferred to use a crude extract of rabbit reticulocytes, or a crude extract of interferon-treated L929 or HeLa cells, as a source of 2-5A synthetase.

The 2-5A synthetase is bound to a column of, for example, agarose through a double-stranded polynucleotide, e.g., poly(rI).poly(rC). The column is washed with a buffer containing aqueous KCl, aqueous magnesium acetate, glycerol and HEPES (pH 7.5). Dithiothreitol is not used, in order to avoid reduction of the azido residues. The nucleoside 5'-triphosphates from which the oligomer is to be formed are charged onto the column in the same buffer and incubated from about 3 to about 18 hours, between about 25° C. and about 35° C., preferably 30° C. The column is then eluted with the buffer.

The material washed from the poly(rI).poly(rC)/2-5A synthetase column is then further purified by application to a DEAE-cellulose column., followed by washing with a wash buffer of 90 mM KCl 20 mM HEPES, pH 7.5. The column is eluted with an elution buffer of 350 mM KCl and 20 mM HEPES, pH 7.5, to isolate a mixture of trimer, tetramer and possibly pentamer (2'-5')azido-oligoadenylate. The individual azido-oligoadenylates are then separated by either DEAE-cellulose chromatography according to the method of Doetsch, et al., Nature 291:355–358 (198), or by high performance liquid chromatography ("HPLC"), according to Lee and Suhadolnik, Biochemistry 24:551–555 (1985). Alternatively, HPLC may be used to purify and separate the azido-oligoadenylate products directly from the eluent of the poly(rI) poly(rC)/2-5A synthetase column.

The core molecules of the (2'-5')azido-oligoadenylates are produced by dephosphoroylating the 5'-position. Any phosphatase or combination of phosphatases effective against terminal phosphate groups, but inert with respect to 2'-5, phosphodiester bonds, may be employed. Thus, there may be utilized bacterial alkaline phosphatase ("BAP"). While BAP will remove all of the phosphate groups at the 5'- position, this removal may, if desired, be carried out in two stages. Utilizing apyrase, ATPase, or pyrophosphatase, the outermost two phosphate groups of a triphosphate moiety, or the outermost phosphate group of a diphosphate moiety, may be removed. Thus, according to this method, 5'-monophosphates may be formed from 5'-triphosphates and 5'-diphosphates of the (2'-5')azidooligoadenylates.

The 5'-terminal phosphate group is advantageously removed according to the procedure of U.S. Pat. No. 4,464,359, the entire disclosure which is incorporated herein by reference.

The 5'-monophosphates of the compounds of the present invention may be prepared by incubating the core azido-oligoadenylate with POCl$_3$ and triethylphosphate, followed by the addition of water and neutralization to pH 7-8. The solution may then be chromatographed by DEAE-Sephadex chromatography to isolate the oligomer 5'monophosphate in essentially 90% yield.

5'-Diphosphate and 5'-triphosphates may be prepared from the corresponding oligomer 5'-monophosphate by dissolving the same in dimethylformamide and dimethylsulfoxide, followed by reaction with triphenylphosphine, imidazole, and dipyridinyl disulfide. The reaction mixture is added to a solution of NaI in acetone, from which is obtained a sodium salt of the 5'-phosphoroimidazolidate oligomer. The salt is dissolved in tri-n-butylammonium pyrophosphate in dimethylformamided the latter then being removed in vacuo. The resulting residue is dissolved in triethylammonium bicarbonate, to form the triethylammonium salt of the oligomer products. The latter consists of a mixture of 5'-mono-, 5'-di- and 5'-triphosphates of the oligomer, which are then separated by DEAE-Sephadex ($A_{25}$) column chromatography.

8-N$_3$ATP used in the following synthetic methods is commercially available from Sigma Chemical Company, St. Louis, Missouri (Cat. No. A$_{2392}$), or may be synthesized from 8-bromo-AMP as described by Czarnecki et al., Methods Enzymol. 56:642–653 (1979). Authentic p$_3$A$_3$ is commercially available from Pharmacia, Inc., NJ, Cat. No. 27-2110-01. 2-N$_3$ATP may be synthesized by preparing 2-azidoadenosine from commercially-available 2-chloroadenosine (Sigma Chemical Company, Cat. No. C5134) according to the procedure of Czarnecki et al., Proc. Natl. Acad. Sci. USA 79:7744–7748 (1982), (described hereinafter in Example 1), followed by 5'-monophosphorylation, according to Yoshikawa et al., Tetrahedron Letters 50:5065–5068 (1967), (described hereinafter in Example 3), and formation of the 5'-triphosphate (Example 4).

2,8-N$_3$ATP may be prepared from 2-chloroadenosine as described in Example 2, followed by 5'-monophosphorylation according to Yoshikawa et al. (Example 3), and formation of the 5'-triphosphate (Example 4).

The synthetic methods for preparing 2-$N_3$ATP and 2,8-$N_3$ATP are described as follows.

EXAMPLE 1

Synthesis of 2-Azidoadenosine

Two mmoles of anhydrous hydrazine are combined with 1-2 mmoles of 2-chloroadenosine (Sigma, Cat. No. $A_{2392}$). The reaction mixture is allowed to stand at room temperature for 16 hours, and then $N_2$ is bubbled through the mixture to remove volatile products. 2-Hydroazidoadenosine is obtained from the mixture by crystallization. To the 2-hydroazidoadenosine crystals are added 7 ml of aqueous acetic acid, 0° C., and 17 ml of 1.2 mM $NaNO_2$, 0° C. The mixture is incubated for ten minutes to give 2-azidoadenosine, which crystallizes out of solution.

EXAMPLE 2

Synthesis of 2,8-Diazidoadenosine

To 0.15 mmoles 2-chloroadenosine are added 2 ml of 1M sodium acetate, pH 3.8, in a 5 ml screw top test tube. To this mixture is added 2 ml of bromine water containing 0.2 micromoles bromine, and the mixture is allowed to stand for 4 hours at room temperature. Unreacted bromine is removed by bubbling air through the reaction mixture. The pH is adjusted to pH 6.8 by addition of 4 M NaOH, and 2-chloro-8-bromoadenosine is crystallized from water and dried. Five mmoles of the crystals are dissolved in 25 ml anhydrous dimethylformamide, followed by the addition of 10 ml lithium azide at 18.C and 5 ml water. The mixture is added to a Dowex 1 hydroxide column (10 ml×1 ml), and then displaced from the column with 70% aqueous methanol. The mixture is evaporated, and 2,8-diazidoadenosine is obtained as crystals.

The 5'-monophosphates of 2-azidoadenosine and 2,8-diazidoadenosine may be prepared according to the method of Yoshikawa et al., Tetrahedron Letters 50:5065–5068 (1967), as described in Example 3.

EXAMPLE 3

5'-Monophosphorylation of Azidoadenosines 6.5 mmole of 2-azidoadenosine or 2,8-diazidoadenosine are added to 13 mmoles $POCl_3$ and 80 mmoles triethylphosphate, and incubated in a sealed vial for 1-5 hours at $-5°$ C. Water is then added to the mixture, which is neutralized with NaOH to pH 7.8. The 5'-monophosphate is isolated from the reactants by adding the solution to a DEAE-Sephadex $A_{25}$ column ($HCO^-_3$ form, 1×28 cm). The 5'-monophosphate (i.e., 2-$N_3$AMP or 2,8-$N_3$AMP) is eluted with a linear gradient of 0.25M–0.75M triethylammonium bicarbonate buffer (pH 7.5, total volume 500 ml) at a flow rate of 35 ml/hour. The product elutes at about 186 ml of eluent in about 90% yield.

2-$N_3$ATP and 2,8-$N_3$ATP may be prepared from 2-$N_3$AMP and 2,8-$N_3$AMP, respectively, by the procedure of Example 4, which gives a mixture of the original 5'-monophosphate, the 5'-diphosphate and the 5'-triphosphate. The triphosphate is isolated from the mixture in about 55% yield.

EXAMPLE 4

Synthesis of Azidoadenosine 5'-Di- and 5'-Triphosphates from the Corresponding Azidoadenosine 5'-Monophosphate 5.2 micromoles of 2-$N_3$AMP or 2,8-$N_3$AMP is dissolved in dry dimethylformamide (50 microliters), and the dimethylformamide is removed in vacuo. The procedure is repeated thrice. The dry residue is dissolved in 250 microliters dimethylformamide and 25 microliters dry dimethylsulfoxide. Triphenylphosphine (6.6 mg, 25 micromoles), imidazole (3.4 mg, 50 micromoles), and dipyridinyl disulfide (5.5 mg, 25 micromoles) are added to the stirred solution. After 5 hours stirring at ambient temperature, the entire reaction mixture is added dropwise to a solution of sodium iodide in acetone (10 microliters of a 1% solution). The colorless precipitate which forms is centrifuged down, washed with dry acetone thrice and finally dried over $P_2O_5$ for 2 hours. The sodium salt of the azidoadenosine 5'-phosphoroimidazolidate is dissolved in dry tri-n-butylammonium pyrophosphate in dimethylformamide (400 microliters). After 36 hours at room temperature, the dimethylformamide is removed in vacuo. The residue is dissolved in 0.25M triethylammonium bicarbonate (pH 7.5, 1 ml). This solution is added to a DEAE-Sephadex $A_{25}$ column ($HCO_3^-$ form, 1×28 cm). The product is eluted with a linear gradient of 0.25M–0.75M triethylammonium bicarbonate buffer (pH 7.5, total volume 500 ml) at a flow rate of 35 ml/hour. The unreacted azidoadenosine 5'monophosphate, and the 5'-di- and 5'-triphosphate thereof, are isolated as triethylammonium salts in yields of about 30%, 15% and 55%, respectively, in the following elution volumes 5'-monophosphate, 110-120 ml; 5'-diphosphate, 150-170 ml; 5'-triphosphate, 180-190 ml.

The (2'-5')azido-oligoadenylate of the present invention may be prepared as 5'-triphosphates from ATP, 2-$N_3$ATP, 8-$N_3$ATP and/or 2,8-$N_3$ATP according to the procedure of Example 5.

EXAMPLE 5

(2'-5')Azido-Oligoadenylate Synthesis

Poly(rI) poly(rC)-agarose columns (0.15×1.5cm) bound with 2-5A synthetase from rabbit reticulocytes lysates are prepared as described in Doetsch et al., Nature 291:355-358 (1981). The column is washed with buffer A, which comprises the following: 8.5 mM HEPES, pH 7.5, 17 mM Mg(OAc)2, 42.6 mM KCl, and 5% glycerol. A reaction mixture containing one or more of the azidonucleotides (2-$N_3$ATP, 8-$N_{N1}$ATP or 2,8-$N_3$ATP) in buffer A is incubated on the column for 3-18 hours at 30° C. The column is eluted with buffer A. The eluent contains azido analogues of 2-5A, i.e., a mixture of dimer, trimer, tetramer and higher (2'-5')azidooligoadenylate 5'-triphosphates.

EXAMPLE 6

Isolation of (2'-5')Azido-Oligoadenylates

A mixture of (2'-5')azido-oligoadenylates is isolated from the eluent of Example 5 by DEAE-cellulose chromatography by the procedure of Doetsch et al. Accordingly, the eluent from the poly(rI) poly(rC)/2-5A synthetase column is applied to a DEAE-cellulose column (Whatman DE52; 0.5×1.7 cm) and washed with 50 ml of buffer B (90 mM KCl and 20 mM HEPES, pH 7.5).

The (2'-5')azido-oligoadenylates (trimer, tetramer and higher 5'-triphosphates) are displaced from the column with 5 ml of buffer C (350 mM KCl and 20 mM HEPES, pH 7.5). Five ml samples of the eluent are collected and dialyzed (45 minutes, 4 L of $H_2O$, 4 times, 0° C.), and lyophilized. The mixture is rechromatographed on the same DEAE-cellulose column (Whatman DE52; 0.5×1.7 cm), and the (2'-5')azido-oligoadenylates are displaced with a 50-150 mM linear gradient of NaCl (40 ml/40 ml) and 50 mM Tris-HCl, pH 8.0, in 7M urea. One-ml fractions are collected at a flow rate of 4 ml/hour. The fractions are dialyzed (45 minutes, 4 L of $H_2O$, 4 times, 0° C.). The various (2'-5')azido-oligoadenylates are thus separated quantitatively by this method, with 95% recovery. Trimer, tetramer and pentamer triphosphates elute at about 25, 35 and 47 ml elution volumes, respectively.

The product obtained according to the method of Example 5 comprises compounds wherein m equals 3 and n equals and 2, predominantly, that is, trimers and tetramers containing 5'-triphosphates. In accordance with the same procedure, compounds where m equals 3 (that is, pentamers) may be also obtained in lesser amounts.

As an alternative to the complete DEAE-cellulose chromatography of Example 6, the (2'-5')azido-oligoadenylates of the invention may be isolated by HPLC directly from the poly(rI).poly(rC)/2-5A synthetase column eluent (Example 5) or from the DEAE-cellulose column eluent eluted with buffer C in Example 6.

EXAMPLE 7

Isolation of (2, 5')Azido-Oligoadenylates by High Performance Liquid Chromatography A (2'-5')azido-oligoadenylate mixture obtained as either (i) the poly(rI).poly(rC)/2-5A synthetase column eluent from Example 5 or (ii) the DEAE-cellulose column eluent obtained by washing that column with buffer C in Example 6, is purified by HPLC according to the method of Lee and Suhadolnik, Biochemistry 24:551-555 (1985). Using a Waters Model 6000 pump equipped with a Model U6K injector and controlled by a Model 660 solvent programmer, reverse phase chromatography is performed with a Waters Radial Compression System (Z-module) and Bondapak Radial-pak cartridge (8 mm×10 cm). For separation, 50 mM ammonium phosphate, pH 7.0 (buffer D) and methanol:water (1:1) (buffer E) are used in a linear gradient (t=1 min., 10% E; t=31 min., 20% E) at a flow rate of 1 ml/min. (2'5')azidoadenylate trimer and tetramer 5'-triphosphates elute from the column at 9.0 minutes and 13.0 minutes, respectively.

The identity of the products may be further confirmed by thin layer chromatography analysis (Eastman Chromagram, 13254) with a solvent comprising isobutyric acid:ammonia: water (66:1:33 (v/v/v)), which reveals ultraviolet 0 35 absorbing regions for oligoadenylate 5'-mono-, di- and triphosphates at $R_f$ 0.66, 0.58 and 0.50, respectively. Product identity may also be confirmed by PEI-cellulose thin layer chromatography (Brinkman) with the solvent 0.25 M ammonium bicarbonate, which reveals ultraviolet absorbing regions for oligoadenylate 5'-mono-, di- and triphosphates at $R_f$ 0.58, 0.38, and 0.19, respectively.

Core compounds of the above prepared (2'-5')azidooligoadenylates may be formed by removing the 5'-terminal triphosphate group according to the following example.

EXAMPLE 8

Enzymatic Dephosphorylation of (2'-5') Azido Oligoadenylate 5'-Triphosphates 2 mM $p3(A_{x\text{-}azido})_3$ in water is added to 1 M Tris-HCl buffer, pH 8.0, to which is added two volumes of glass distilled water and bacterial alkaline phosphatase (Sigma) to ⅛ of the total volume of the reaction mixture. The reaction mixture is incubated at 37° C. for 90 minutes and then is washed through a DEAE-Sephadex $A_{25}$ column ($HCO_3^-$ form, 1×28 cm). The product is eluted with a linear gradient of 0.25M–0.75M triethylammonium bicarbonate buffer (pH 7.5'total volume 500 ml) at a flow rate of 35 ml/hour. The desired 5'-dephosphoroylated trimer core molecule $(A_{x\text{-}azido})_3$ elutes as a triethylammonium salt at about 110 ml eluent.

In accordance with the same procedure, where m is 1 or 2 and n is 0, 1, 2, or 3, there is obtained the corresponding 5'-dephosphoroylated oligomer having an d n value. For example, following the same procedure of Example 8, the tetramer core compounds of the invention elute at about 130 ml eluent.

EXAMPLE 9

5'-Monophosphorylation of Core (2'-5')Azido-Oligoadenylates

·6.5 micromoles of a core (2'-5')azido-oligoadenylate (i.e., core dimer, core trimer, core tetramer or core pentamer) are added to 13 micromoles $POCl_3$ and 80 micro moles of triethylphosphate, and incubated in a sealed vial for 1–5 hours at −5° C. Water is then added to the mixture, which is then neutralized with NaOH to pH 7–8. The mixture is added to a DEAE-Sephadex $A_{25}$ column ($HCO_3^-$ form, 1×28 cm). The product is eluted with a linear gradient of 0.25M–0.75M triethylammonium bicarbonate buffer (pH 7.5, total volume 500 ml) at a flow rate of 35 ml/hour. 5'-Monophosphate trimers elute at about 190–200 ml, while 5'monophosphate tetramers elute at about 260–280 ml.

Dimers of the compounds of the present invention (i.e., where n=0) are formed by following the procedure of Example 5 up to the step of elution of the poly(rI) poly(rC)/2-5A synthetase column with buffer A, which eluent contains a mixture of dimer, trimer, pentamer and possibly higher (2'-5')azido-oligoadenylates. The dimer is isolated from the mixture by high performance liquid chromatography according to the procedure of Example 7. The dimer is observed to elute at about 6 minutes elution time in HPLC. It should be noted that the (2'-5')azidoadenylate dimers may not be isolated according to the DEAE-cellulose procedure of Example 6 since they have insufficient charge to remain on the column through washing with buffer B (90 mM KCl and 20 mM HEPES, pH 7.5).

While the above synthetic procedures yield (2'-5')azido-oligoadenylates in the form of triethylammonium salts, other salts, e.g., the corresponding potassium or sodium salts, may be obtained by the simple expedient of a double salt displacement using KCl or NaCl, respectively.

Oligomers containing more than one nucleoside species may be prepared by incubating the corresponding nucleotides with 2-5A synthetase according to Example 5 and isolating the desired (2'-5')azido-oligoadenylate.

Where ATP is reacted with x-N$_3$ATP in a molar ratio of 1:500, respectively, the azido-ATP analog forms the 5'-terminus of the resulting oligomer. Thus, for example, the reaction of x-N$_3$ATP and ATP (500:1) yields a mixture of the following dimer, trimer, and possibly tetramer 5'-triphosphates: p$_3$A$_{x\text{-}azido}$A; p$_3$A$_{x\text{-}azido}$A$_2$ and p$_3$A$_{x\text{-}azido}$A$_3$.) The products are readily separated by DEAE-cellulose chromatography as described in Example 6. Any separated product, e.g. dimer, trimer, etc., can be further incubated with proper molar ratios of either ATP or x-N$_3$ATP according to Example 5 to produce additional oligomers of the present invention.

Where ATP and x-N$_3$-ATP are combined in the presence of 2-5A synthetase, the authentic ATP forms the 5'-terminus, and only one mole of x-N$_3$-ATP adds to the 2'terminus. The resulting p$_3$AA$_{x\text{-}azido}$ dimer is isolated by HPLC as described above. The p$_3$AA$_{x\text{-}azido}$ dimer may then be incubated with a 500 molar excess of ATP to give a mixture comprising the unreacted dimer, p$_3$AA$_{x\text{-}azido}$A, and possibly p$_3$AA$_{x\text{-}azido}$A$_2$.

If the authentic 2-5A dimer triphosphate p$_3$A$_2$ is reacted with x-N$_3$ATP, a single mole of ATP analog adds to the 2'-terminus of the dimer to provide p$_3$A$_2$A$_{x\text{-}azido}$.

These and other reactions and their pruducts are set forth in the following table.

TABLE I

| Reactants | | Molar Ratio | |
|---|---|---|---|
| a | b | a:b | Products |
| x-N$_3$ATP | ATP | 500:1 | p$_3$A$_{x\text{-}azido}$A |
| | | | p$_3$A$_{x\text{-}azido}$A$_2$ |
| | | | p$_3$A$_{x\text{-}azido}$A$_3$ |
| x-N$_3$ATP | ATP | 1:1 | p$_3$AA$_{x\text{-}azido}^1$ |
| | | | p$_3$AA$_{x\text{-}azido}$A$^1$ |
| | | | p$_3$AA$_{x\text{-}azido}$A$_2^1$ |
| x-N$_3$ATP | p$_3$A$_2$ | 1:1 | p$_3$A$_2$A$_{x\text{-}azido}$ |
| x-N$_3$ATP | p$_3$A$_3$ | 1:1 | p$_3$A$_2$A$_{x\text{-}azido}$ |
| p$_3$(A$_{x\text{-}azido}$)$_2$ | ATP | 1:1 | p$_3$(A$_{x\text{-}azido}$)$_2$A$^2$ |
| p$_3$A$_2$A$_{x\text{-}azido}$ | ATP | 1:500 | p$_3$A$_2$A$_{x\text{-}azido}$A$^2$ |
| p$_3$A$_2$A$_{x\text{-}azido}$ | ATP | 1:1 | p$_3$A$_2$A$_{x\text{-}azido}$A |
| p$_3$(A$_{x\text{-}azido}$)$_3$ | ATP | 1:500 | p$_3$(A$_{x\text{-}azido}$)$_3$A$^2$ |
| p$_3$AA$_{x\text{-}azido}$A | x-N$_3$ATP | 1:500 | p$_3$AA$_{x\text{-}azido}$AA$_{x\text{-}azido}$ |
| p$_3$(A$_{x\text{-}azido}$)$_4$ | ATP | 1:500 | p$_3$(A$_{x\text{-}azido}$)$_4$A$^2$ |

$^1$Obtained by isolating p$_3$AA$_{x\text{-}azido}$ and reincubating with a 500 molar excess of ATP.
$^2$Chain extension by further addition of adenylyl moieties to the 2'-terminus is possible depending on the time of incubation of the reaction mixture with 2-5A synthetase.

It may be readily appreciated that oligonucleotides containing more than one azido-nucleotide species may be prepared by the herein described methods. For example, following preparation of the dimer 5'-triphosphate p$_3$A$_{2azido}$A2-azido, incubation of the same with an equimolar concentration of 8-N$_3$ATP yields a mixture of, essentially, p$_3$(A$_{2\text{-}azido}$)$_2$A$_8$-azido and p$_3$(A$_{2\text{-}azido}$)$_2$-(A$_{8\text{-}azido}$)$_2$, which mixture can be separated into its component products by the methods described herein.

Biological Activity

It is generally regarded that activation of RNase L by 2-5A is key to the antiviral defense mechanisms. Interferon induces 2-5A synthetase which produces 2',5'linked oligoadenylates upon activation by double-stranded RNA. The only known biochemical effect of 2-5A is activation of RNase L. The latter enzyme hydrolyses mRNA and rRNA, thereby resulting in inhibition of protein synthesis. The activation of RNase L is transient unless 2-5A is continuously synthesized, since 2-5A is rapidly degraded. RNase L activation thus plays a critical role in inhibiting replication, and therefore in defending against infection by viruses. The compounds of the invention bind to and activate RNase L, as shown by the following experiments.

RNase L Binding by 8-Azido-p$_3$A$_3$

RNase L was obtained from L929 cells by the following procedure. The L929 cells were maintained in monolayer culture in Dulbecco's modified Eagle medium supplemented with 5% bovine serum. Monolayers were tested with 200 units/ml of mouse interferon for 20 hours. Cell extracts of the L929 cells were prepared by collecting the cells by trypsinization, washing them once with phosphate-buffered saline and lysing the cells in NP40 buffer according to the method of Silverman, et al., Eur. J. Biochem. 124:131–138 (1982).

The ability of 8-azido-p$_3$A$_3$ to compete with p$_3$A$_4$-[$^{32}$P]pCp for binding to RNase L in the L929 cell extracts was compared to p$_3$A$_3$ using radiobinding assays (50 micrograms of protein/assay) according to the method of Knight et al., Methods Enzymol. 79:216–227 (1981). 8-Azido-p$_3$A$_3$ inhibited p$_3$A$_4$[$^{32}$P]pCp binding to RNase L in a concentration dependent manner (FIG. 1A). 8-Azido-p$_3$A$_3$ (FIG. 1A, solid circle data points) binds to RNase L with an IC$_{50}$ of 2×10$^{-9}$M, which is equivalent to the IC$_{50}$ of authentic p$_3$A$_3$ (FIG. 1A, solid triangle data points).

RNase L Activity by 8 Azido-p$_3$A$_3$ (Core-Cellulose Assay)

The recently developed core cellulose assay of Silverman, Anal. Biochem. 144:450–460 (1985), which involves the immobilization and partial purification of RNase L on 2-5A core-cellulose, was used to measure the ability of 8-azido-p$_3$A$_3$ to activate RNase L. For this purpose, poly(U)[$^{32}$P]pCp was synthesized from poly(U) using T4 RNA ligase, as described by Silverman. The results are set forth in FIG. 1B. 8-Azido-p$_3$A$_3$ (solid circle data points) was equipotent to authentic p$_3$A$_3$ (solid triangle data points, FIG. 1B) in its ability to activate RNase L to hydrolyze the substrate poly(U)[$^{32}$P]pCp to acid-soluble fragments (IC$_{50}$, 7 . 10$^{-9}$M).

RNase L Activation by 2- and 8-Azido-p$_3$A$_3$ (rRNA Cleavage Assay)

Figure 2:
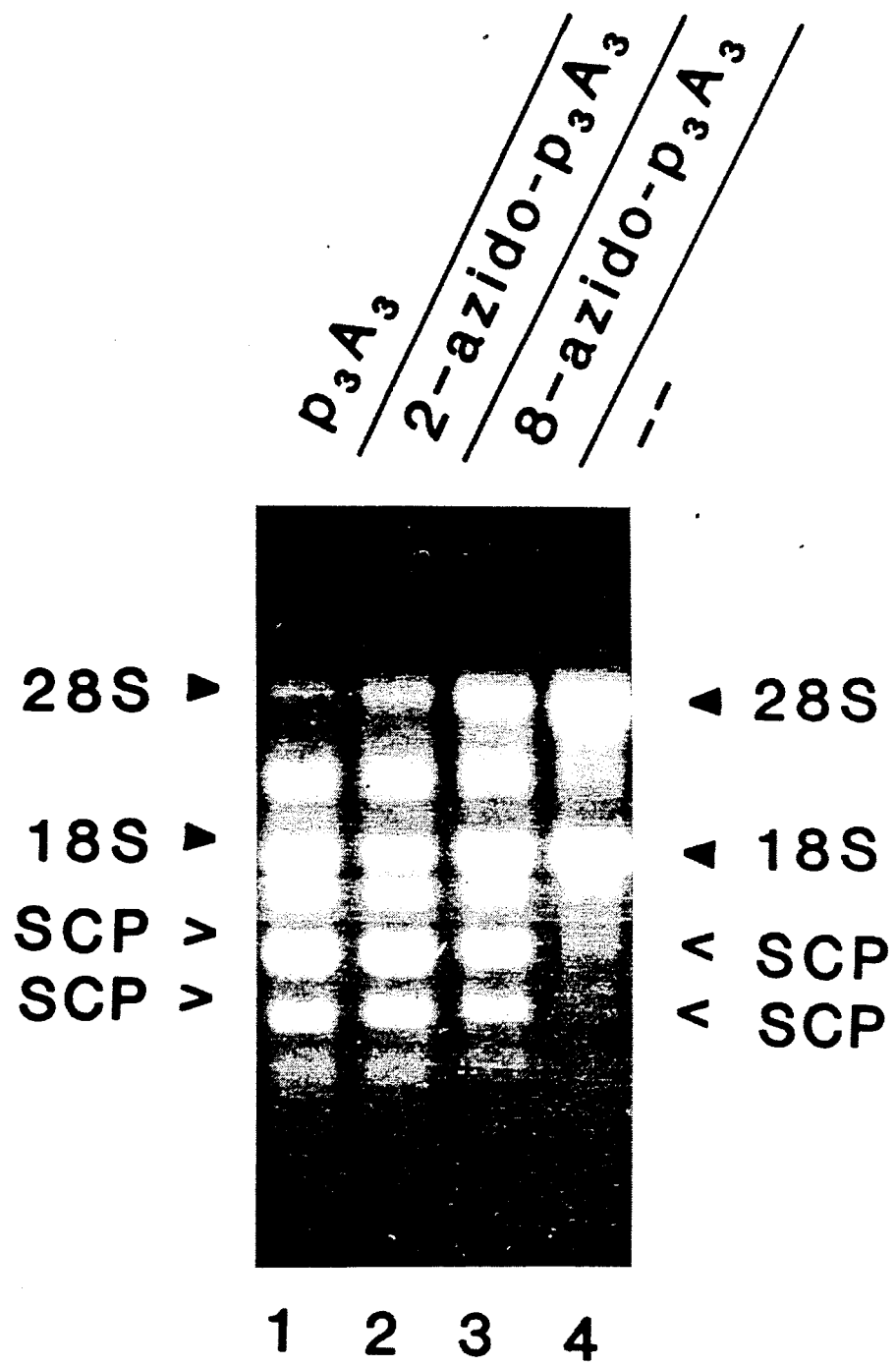
FIG. 2 represents a rRNA cleavage assay with 2-azido-$p_3A_3$ and 8-azido-$p_3A_3$ L929 cell extracts were incubated in the absence (lane 4) or presence of $p_3A_3$ (lane 1), 2-azido-$p_3A_3$ (lane 2), or 8-azido-$p_3A_3$ (lane 3) at $1 \times 10^{-8}$ M final concentrations. The positions of 28S and 18S rRNA, and the positions of RNase L specific cleavage products ("SCP"), are indicated.

Activation of RNase L by the compounds of the invention was also measured in a ribosomal RNA cleavage assay using L929 cell extracts. The extracts were prepared in glycerol buffer in 15 microliters final volume as described by Kariko et al., Biochem. Biophys. Res. Commun. 128:695–698 (1985). As shown in FIG. 2, 2- and 8-azido-p$_3$A$_3$, at final concentrations as low as 10$^{-9}$M, activated RNase L to degrade rRNA to its highly characteristic, specific cleavage products. The degradation was concentration dependent. 2- and 8-Azido-p$_3$A$_3$ where as potent as authentic p$_3$A$_3$ in this regard.

Photoaffinity Labelling of 2-5A Binding Proteins by (2'-5')Azido-Oligoadenylates The (2'-5')azido-oligoadenylates, upon exposure to low intensity ultraviolet light, readily form nitrene free radical intermediates. They are thus capable of covalent photoinsertion into and/or cross-linking of a variety of biological molecules. Cross-linking may occur between two or more biological molecules. Thus, in addition to inhibiting viruses by activating host cell RNase L, the compounds of the present invention may act to inhibit viruses by photoinsertion into, or cross-linking of, viral biological molecules.

The (2'-5')azido-oligoadenylates, following insertion into the 2-5A binding site on RNase L, may be photoactivated and induced to covalently cross-link to the RNase L molecule, according to the following reaction:

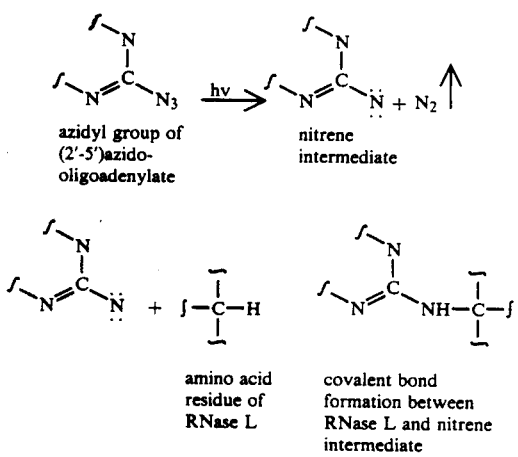

With this in mind, the following experiment was performed to demonstrate the covalent cross-linking effect of the (2'-5')azido-oligoadenylates on several 2-5A binding proteins from L929 cells, which binding proteins are believed to be forms of RNase L:

Ten microliters of L929 cell extracts (100 micrograms protein/assay) were combined with 10 microliters of a buffer (140 mM NaCl, 35 mM Tris-HCl, pH 7.5) and were incubated in the presence of $1 \times 10^{-6}$ M [gamma-$^{32}$p]2-azido -p$_3$A$_3$ (0.9 microCi/nmol) or $1 \times 10^{-6}$M [alpha-$^{32}$p]8-azido -p$_3$A$_3$ (0.9 microCi/nmol) or $1 \times 10^{-9}$M p$_3$A$_4$[$^{32}$P]pCp (3 mCi/nmol) in a 30 microliter final volume. The samples, after incubation in microcentrifuge tubes at 0° C. for 90 minutes, were transferred into ice-mold porcelain spot plates and photolysed for 60 seconds using a 254 nm UVG-11 Mineralight lamp (Ultraviolet Products, Inc.) at a distance of 2 cm (1.0 J/m$^2$). Sixty microliters of a reductive, protein-solubilizing mixture (15.4 mg/ml dithiothreitol, 25% w/v sucrose, 2.5% sodium dodecylsulfate, 25 mM TrisHCl, pH 8.0, 0.0025% pyronine Y) were added to the samples. Photo-incorporation of the $^{32}$P-labeled 2-azido-p$_3$A$_3$ and 8-azido-p$_3$A$_3$ into the L929 protein was determined by SDS-PAGE (Lamelli, Nature (London) 227:680-685 (1970)). The SDS-PAGE gels were stained with Coomassie blue, dried and subject to autoradiography at −70° C. with X-Omat film (Kodak).

Figure 3A:
FIG. 3A is an autoradiogram following SDS-PAGE of interferon-treated L929 cell extracts incubated with [gamma-$^{32}$P]2-azido-$p_3A_3$ at $1 \times 10^{-6}$ M in the absence (lane 1) or presence of $p_3A_3$ at $1 \times 10^{-5}$ M and $1 \times 10^{-4}$ M (lanes 2 and 3, respectively). The samples were UV-irradiated for 60 seconds at 0° C. prior to electrophoresis. Photolabelled proteins were detected by autoradiography. Molecular weight standards are indicated.
Figure 3B:
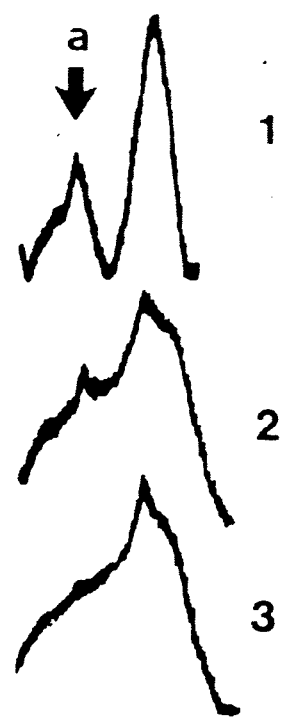
FIG. 3B comprises densitometric traces of a portion of the FIG. 3A autoradiogram. Authentic $p_3A_3$ is shown to inhibit the covalent cross-linking of [gamma-$^{32}$P]2-azido-$p_3A_3$ to a protein (a) indicated by the arrow.
Figure 4B:
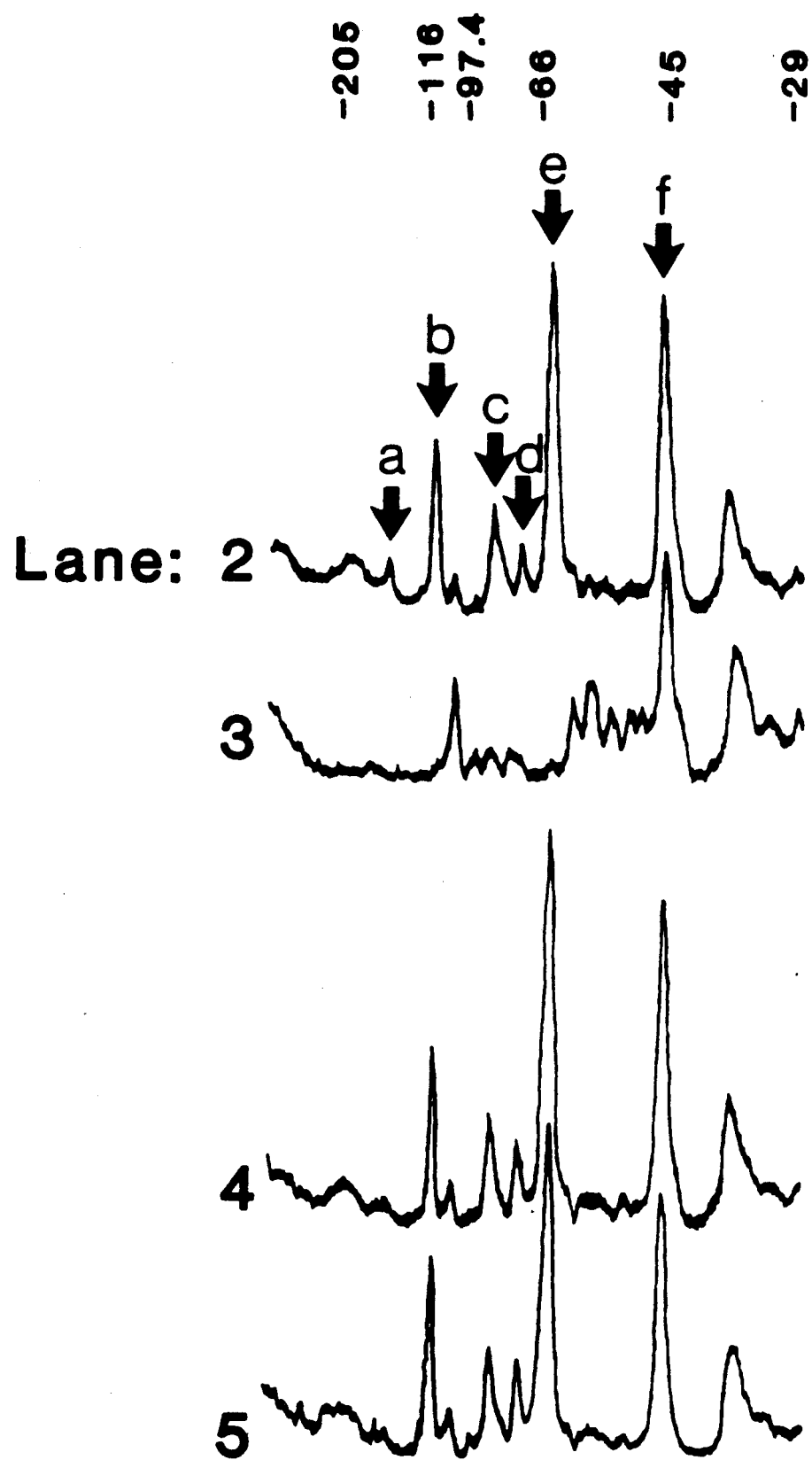
FIG. 4B comprises densitometric traces of lanes 2–5 of the FIG. 4A autoradiogram. The arrows indicate the positions of proteins whose photolabelling are inhibited by $p_3A_3$ (i.e., proteins a–f). Molecular weight standards ($\times 10^3$) are indicated.

As shown in FIG. 4, lanes 1 and 2, photo-crosslinking by photo-activated 2-azido-p$_3$A$_3$ and 8-azido-p$_3$A$_3$ was UV radiation-dependent, found to be maximal after 60 seconds UV exposure (lanes 1 and 2). As shown in FIG. 3, photolabelling of a 185,000 dalton protein (lane 1, proteina) by [gamma-$^{32}$P]2-azido-p$_3$A$_3$ was specifically inhibited by p$_3$A$_3$ (FIG. 3, lanes 2 and 3). The 185,000 dalton protein is believed to be RNase L. Other proteins were also photolabelled by [gamma-$^{32}$P]2-azido-p$_3$A$_3$, but such photolabelling was not inhibited by authentic p$_3$A$_3$ in a dose dependent manner (FIG. 3, lanes 1-3).

Similar photolabelling experiments with [alpha-$^{32}$P]8-azido-p$_3$A$_3$ resulted in photolabelling of six proteins (a–f) in interferon-treated L929 cell extracts (FIG. 4, lane 2).

In competition experiments, photolabelling of proteins a–f was inhibited by the addition of authentic p$_3$A$_3$ at $1 \times 10^{-4}$M final concentration (FIG. 4, lane 3). This photo-incorporation of proteins a–f was specific for p$_3$A$_3$, because A$_3$ or (3'-5')A$_3$ at $5 \times 10^{-4}$M final concentration did not prevent covalent photo-insertion (FIG. 4, lanes 4 and 5). Under identical experimental conditions, p$_3$A$_4$[$^{32}$P]pCp covalently photo-inserted into one protein with a molecular weight of 80,000 (FIG. 4, lane 6).

The data presented herein (FIGS. 3 and 4) conclusively show that UV-activated 2- and 8-azido analogues of 2-5A can specifically cross-link to at least seven 2-5A binding proteins of molecular weights 46,000–185,000. The binding proteins are believed to be forms of RNase L. Under identical experimental conditions, p$_3$A$_4$[$^{32}$P]pCp photo-inserted to only one protein with a molecular weight of 80,000 (FIG. 4, lane 6).

While it might be expected that the 2- and 8-azido analogues of 2-5A would photolabel the same proteins, it was found that [gamma-$^{32}$P]2-azido-p$_3$A$_3$ was specifically photoincorporated into only one protein with a molecular weight of 185,000 (FIG. 3, protein a), whereas [alpha$^{32}$P]8-azido-p$_3$A$_3$ specifically cross-linked to six proteins with molecular weights of 46,000–158,000 (FIG. 4, proteins a–f).

Prior to the present invention, only one 2-5A binding protein (RNase L) of about molecular weight 185,000 has been reported. The present invention has revealed six additional 2-5A binding proteins (proteins a–f) which may be different forms of RNase L.

In situ photoactivation of the (2'-5')azido-oligoadenylates following binding to RNase L does not interfere with RNase L activity, as established by the following experiment:

Ten microliters of L929 cell extract (100 microgram protein/assay) were combined with ten microliters buffer (140 mM NaCl, 35 mM Tris-HCl, pH 7.5) and were incubated in the presence of $1 \times 10^{-6}$M 8-azido-p$_3$A$_3$ in a 30 microliter final volume. The sample was transferred to ice-cold porcelain spot plates and photolysed for 60 second using a 254 nm UVG-11 Mineralight lamp at a distance of 2 cm (1.0 J/m$^2$) to photolabel the RNase L/8-azido-p$_3$A$_3$ complex. A ribosomal RNA cleavage assay was performed as described above, but using the photolabelled complex. The latter was observed to cleave 18S and 28S rRNA to the same specific cleavage products characteristic of RNase L activation by 8-azido-p$_3$A$_3$ without photoactivation (FIG. 2).

For pharmaceutical use, the compounds of the invention may be taken up in pharmaceutically acceptable carriers, such as, solutions, suspensions, tablets, capsules, ointments, elixirs and injectable composition and the like. They may be administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be useful in treating or protecting humans and animals from viral infections such as Herpes simplex, rhinovirus, Epstein Barr virus, measles virus, multiple sclerosis (which may be caused by a viral agent) and the various human T-cell leukemia viruses ("HTLV") such as HTLV-I, which causes cutaneous T-cell lymphoma, HTLV-II, which causes Sezary lymphoma, and HTLV-III (also known as "HIV-1"), which is responsible for acquired immune deficiency syndrome ("AIDS").

The compounds possess antiviral activity against plant-infecting virus, particularly tobacco mosaic virus. Similar results may be obtained against other viruses which cause necrosis in turnips, cucumber, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a suitable carrier material. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasma. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants are effectively treated with an aqueous formulation containing from about $10^{-1}$ to about $10^{-2}$M concentration of active ingredient. The compounds of the invention may be applied at very low concentrations. An effective amount of active ingredient on the plant surface is from about $10^{-8}$ to about $10^{-12}$ mole per cm2 of plant surface area, with about $10^{-10}$ mole to about $10^{-12}$ mole per cm$^2$ being preferred. For the typical tobacco plant of 1,000 cm$^2$, $10^{-5}$M of compound is effective. At this rate, one pound of active ingredient is sufficient to treat $2 \times 10^8$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents.

Adenosine, adenine, or other purine or pyrimidine nucleoside or other aromatic organic bases, are particularly useful as UV-stabilizers. These molecules absorb UV light and may therefore, when combined with the (2'-5')azido-oligoadenylates, protect against premature photoactivation of those compounds. Once on the plant, the aromatic organic bases are rapidly taken up by the stroma, exposing the antiviral agent to the effect of the sun's UV irradiation, thereby resulting in photoactivation.

Proteins rich in the aromatic amino acids phenylamine, tryptophan and/or tyrosine comprise another group of useful UV-stabilizers. The antiviral compounds of the invention are photoactivated by sun light as the protein is degraded.

While the (2'-5')azido-oligoadenylates may be administered in the absence of a UV-stabilizer, in such instances it is preferred that the application does not occur during peak daylight hours so as to avoid premature photo-activation of the compound during spraying.

The molar ratio of (2'-5')azido-oligoadenylate to UV-stabilizer in the spraying compositions may be from about 1:50 to about 1:100.

The present invention may be embodied in other specific forms without departing from the spirit or essential attributes thereof and, accordingly, reference should be made to the appended claims, rather than to the foregoing specification, as indicating the scope of the invention.

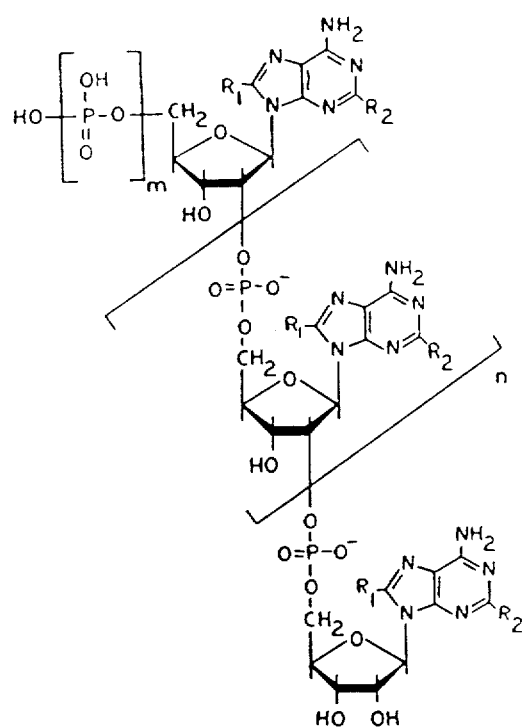

I claim:

1. A compound of the formula wherein m is an integer from 0 to 3, n is an integer from 0 to 3, and each $R_1$ and each $R_2$ is, independently of each other $R_1$ and $R_2$, hydrogen or $N_3$, provided at least one $R_1$ or $R_2$ is $N_3$; and water soluble salts thereof.

2. A compound according to claim 1 wherein n is 1.
3. A compound according to claim 1 wherein n is 2.
4. A compound according to claim 2 wherein m is 3.
5. A compound according to claim 3 wherein m is 3.
6. A compound according to claim 2 wherein m is 0.
7. A compound according to claim 3 wherein m is 0.
8. A compound according to claim 1 wherein $R_1$ is hydrogen and $R_2$ is $N_3$.
9. A compound according to claim 2 wherein $R_1$ is hydrogen and $R_2$ is $N_3$.
10. A compound according to claim 3 wherein $R_1$ is hydrogen and $R_2$ is $N_3$.
11. A compound according to claim 4 wherein $R_1$ is hydrogen and $R_2$ is $N_3$.
12. A compound according to claim 5 wherein $R_1$ is hydrogen and $R_2$ is $N_3$.
13. A compound according to claim 6 wherein $R_1$ is hydrogen and $R_2$ is $N_3$.
14. A compound according to claim 7 wherein $R_1$ is hydrogen and $R_2$ is $N_3$.
15. A compound according to claim 1 wherein $R_1$ is $N_3$ and $R_2$ is hydrogen.
16. A compound according to claim 2 wherein $R_1$ is $N_3$ and $R_2$ is hydrogen.
17. A compound according to claim 3 wherein $R_1$ is $N_3$ and $R_2$ is hydrogen.
18. A compound according to claim 4 wherein $R_1$ is $N_3$ and $R_2$ is hydrogen.
19. A compound according to claim 5 wherein $R_1$ is $N_3$ and $R_2$ is hydrogen.
20. A compound according to claim 6 wherein $R_1$ is $N_3$ and $R_2$ is hydrogen.
21. A compound according to claim 7 wherein $R_1$ is $N_3$ and $R_2$ is hydrogen.
22. A method of controlling a viral infection in mammals comprising administering an antiviral effective amount of a compound according to claim 1.
23. A method of controlling a viral infection in plants comprising administering an antiviral effective amount of a compound according to claim 1.
24. A method according to claim 23 for controlling tobacco mosaic virus.

* * * * *

UNITED STATES PATENT AND TRADEMARK OFFICE
CERTIFICATE OF CORRECTION

PATENT NO. : 4,990,498

DATED : February 5, 1991

INVENTOR(S) : Robert J. Suhadolnik

It is certified that error appears in the above-identified patent and that said Letters Patent is hereby corrected as shown below:

Column 1, line 54, change "2,8-N3ATP" to --2,8-$N_3$ATP--; Col. 1, line 63, change "2-N3ADP, 8-N3ADP and 2,8-N3ADP" to --2-$N_3$ADP, 8-$N_3$ADP, and 2,8-$N_3$ADP--; Col. 1, l. 64, change "x-N3AMP" to --x-$N_3$AMP--; Col. 1, l. 65, change "2-N3AMP, 8-N3AMP and 2,8-N3AMP" to --2-$N_3$AMP, 8-$N_3$AMP and 2,8-$N_3$AMP--; Col. 1, l. 66, change "2-azido-p3A3 or p3(A2-azido)3" to --2-azido-$p_3A_3$ or $p_3(A_2$-azido$)_3$:--; Col. 1, l. 67, change "(2,-5,)2-azidoadenylyl(2,-5,)" to --(2'-5')2-azido-adenylyl(2'-5')--; Col. 2, l. 1, change "8-azido-p3A3 or p3(A8-azido)3" to --8-azido-$p_3A_3$ or $p_3(A_8$-azido$)3$:--; Col. 2, l. 6, change "8-azidoade-" to --2,8-azidoade- --; Col. 3, l. 58, insert a period after "$A_3$"; Col. 4, l. 30, change "RNas L" to --RNase L--; and change "oligoadehylates" to --oligoadenylates--; Col. 4, l. 41, change "(2'5')" to --(2'-5')--; Col. 4, l. 54, insert a --'-- after "N"; Col. 4, l. 66, add immediately after "2-" --azidoadenylyl(2'-5')2-azidoadenylyl(2'-5')2-azidoadenylyl(2'-5')2--; Col. 4, l. 66, change "azidoadazido-adenosine" to --azidoadenosine--; Col. 5, l. 3, insert a hyphen between "8" and "azidoadenosine"; Col. 5, l. 12, insert --azidoadenylyl-- between "2-" and "(2'-"; Col. 6, l. 6, insert --'-- between "(rI)" and "poly"; Col. 6, l. 22, insert a hyphen between "azido" and "oligoadenylates";

UNITED STATES PATENT AND TRADEMARK OFFICE
CERTIFICATE OF CORRECTION

PATENT NO. : 4,990,498

DATED : February 5, 1991

INVENTOR(S) : Robert J. Suhadolnik

Page 2 of 4

It is certified that error appears in the above-identified patent and that said Letters Patent is hereby corrected as shown below:

Col. 6, l. 53, change "(Cat. No. $_{2392}$)" to --(Cat. No. 2392)--; Col. 7, l. 11, change "(Cat. No. $_{2392}$)" to --(Cat. No. 2392)--; Col. 8, l. 35, insert --:-- after "volumes"; Col. 8, l. 51, change "(OAc)2" to --(OAc)$_2$--; Col. 8, l. 53, change "8-N$_{N1}$ATP" to --8-N$_3$ATP--; Col. 8, l. 58, insert a hyphen between "azido" and "oligoadenylate"; Col. 8, l. 65, insert --'-- after "(rI)"; Col. 9, l. 20, insert --1-- after "equals"; Col. 9, l. 59, delete "0 35" after "ultraviolet"; Col. 10, l. 8, change "p3" to --p$_3$--; Col. 10, l. 23, change " d n value" to --unchanged n value--; Col. 10, l. 47, insert --'-- between "(rI)" and "poly"; Col. 11, l. 24, change "pruducts" to --products--; Col. 11, l. 36, (TABLE 1), change "A$_2$" to --A$_3$--; Col. 12, l. 28, change "Activity" to --Activation--: Col. 13, l. 61, change "proteina" to --protein a;

UNITED STATES PATENT AND TRADEMARK OFFICE
CERTIFICATE OF CORRECTION

Page 3 of 4

PATENT NO. : 4,990,498

DATED : February 5, 1991

INVENTOR(S) : Robert J. Suhadolnik

It is certified that error appears in the above-identified patent and that said Letters Patent is hereby corrected as shown below:

Replace the chemical structures at Col. 3, 1. 1-37, and Col. 16, 1. 26-64 with the structure on the attached sheet.

Signed and Sealed this

Sixteenth Day of March, 1993

*Attest:*

STEPHEN G. KUNIN

*Attesting Officer*     Acting Commissioner of Patents and Trademarks